United States Patent
Pakszys

(10) Patent No.: US 6,579,245 B1
(45) Date of Patent: Jun. 17, 2003

(54) DEVICE FOR UNDERPRESSURING COLLECTION AND DOSAGE LIQUID SAMPLES, IN PARTICULAR FOR ANALYTIC TESTS

(75) Inventor: Waldemar Pakszys, Warszawa (PL)

(73) Assignee: P. Z. "HTL"Spolka Akcyjna, Warsaw (PL)

(*) Notice: Subject to any disclaimer, the term of this patent is extended or adjusted under 35 U.S.C. 154(b) by 250 days.

(21) Appl. No.: 09/684,439

(22) Filed: Oct. 10, 2000

(30) Foreign Application Priority Data

Oct. 11, 1999 (PL) .................................................. 335924

(51) Int. Cl.⁷ .............................. A61B 5/00; B65D 81/00

(52) U.S. Cl. ........................ 600/579; 600/576; 604/205; 604/240

(58) Field of Search ................................. 600/573, 575, 600/576, 577, 579, 580, 583, 584; 604/403, 404, 411, 412, 443, 414, 415, 6.15, 19, 187, 245, 246, 247, 198, 199.201, 205, 239–243; 422/99, 101–104

(56) References Cited

U.S. PATENT DOCUMENTS

| | | | | |
|---|---|---|---|---|
| 4,154,229 A | * | 5/1979 | Nugent | 600/577 |
| 4,207,870 A | * | 6/1980 | Eldridge | 137/197 |
| 4,307,731 A | | 12/1981 | Kaufman | |
| 4,421,123 A | | 12/1983 | Percarpio | |
| 4,998,920 A | * | 3/1991 | Johnson | 604/198 |
| 5,356,392 A | * | 10/1994 | Firth et al. | 600/576 |
| 5,897,508 A | | 4/1999 | Konrad | |
| 6,004,278 A | * | 12/1999 | Botich et al. | 600/576 |

FOREIGN PATENT DOCUMENTS

| EP | 0 191 945 | 8/1986 |
|---|---|---|
| WO | WO 95/16395 | 6/1995 |

* cited by examiner

Primary Examiner—Charles A. Marmor, II
(74) Attorney, Agent, or Firm—Michael D. Bednarek; Shaw Pittman LLP

(57) ABSTRACT

A device including a holder with a blood sample collection tube-syringe on the one side and a needle on the other side. An exemplary holder includes a set of two valves. The first valve is on the tube-syringe's side and is a tire valve including an inner needle covered by a tire. The second valve is on the side of the needle and is a membrane valve which has a membrane placed on an under-support with side-inlets.

20 Claims, 6 Drawing Sheets

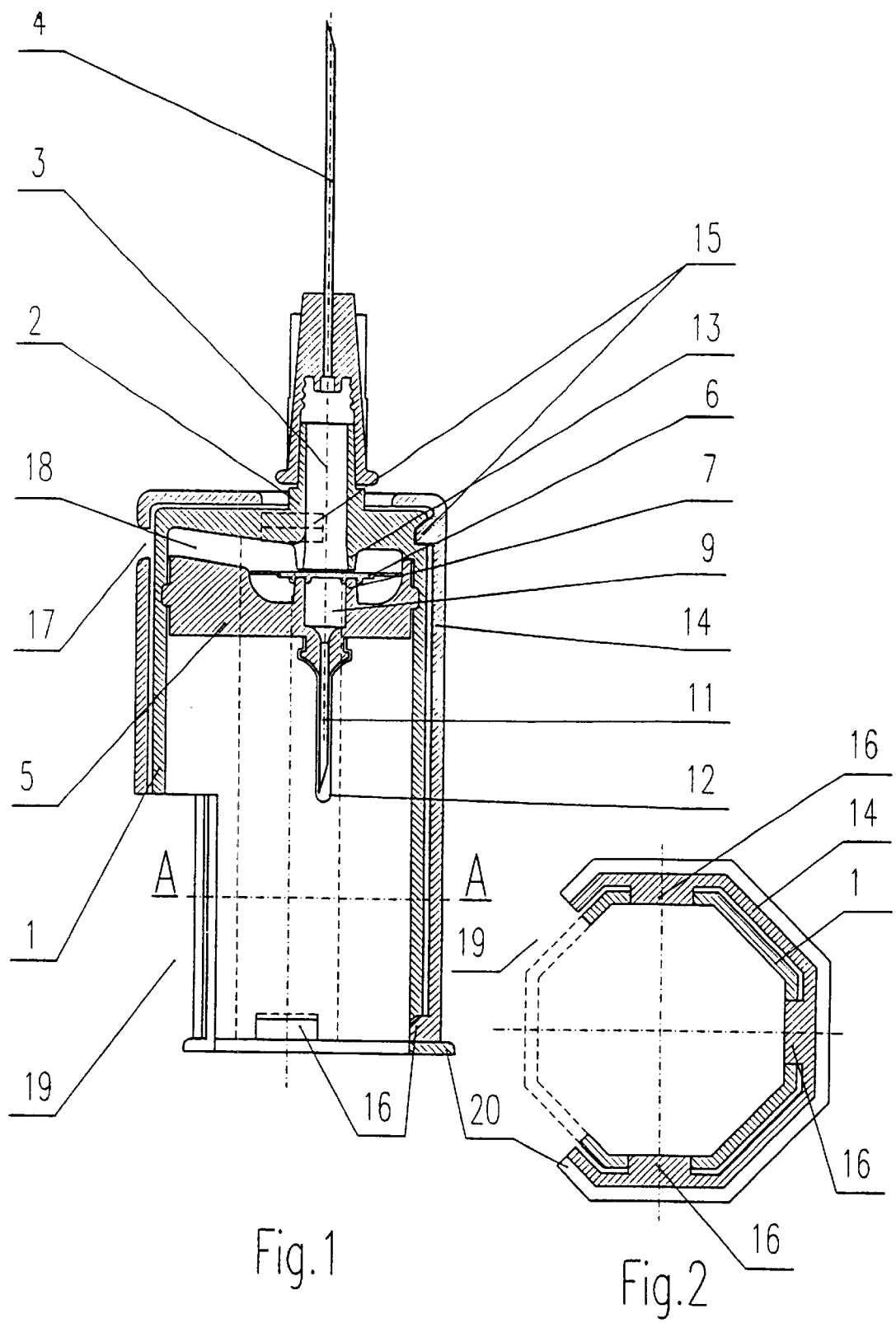

DEVICE FOR UNDERPRESSURING COLLECTION AND DOSAGE LIQUID SAMPLES, IN PARTICULAR FOR ANALYTIC TESTS

BACKGROUND OF THE INVENTION

1. Field of the Invention

This invention relates to a device for underpressuring collection and dosage liquid samples, in particular for collection blood samples from a patient's vein for analytic tests or dosage remedy liquids into a blood vascular system or any body cavity.

2. Description of the Related Art

The European patent No. 0191945 discloses a blood sampling device comprising a cylindrical sample tube and slidable therein a plunger and also comprising an end cap on which there is eccentrically disposed an axially directed cone. The device comprises an adapter fitted on the cone and having two cannulae secured thereon, the outer cannula being free for introduction into a vein while the inner cannula is closed by a tyre valve. The device comprises also a non-return valve which is disposed in the end cap and which consists of an elastically deformable diaphragm having a central valve aperture and a cylindrical support ring for the diaphragm, said ring being inserted into the end cap, the diaphragm and the support ring being constructed as a one-piece diaphragm ring and the diaphragm being disposed in the support ring so as to be inwardly offset and being externally formed as a spherical segment such as to project somewhat beyond the edge of its support ring and a circular valve seat integrally formed concentrically on the inside of the end cap.

Further, the publication of the international application No. WO 95/16395 discloses a holding fixture for a blood sample collection tube of a blood-taking device which has a collecting container, with needle carrier, for a front end of the blood sample collection tube, which is closed off by a closure device. Mounted in the needle carrier is a syringe directed toward the opened end of the collecting container and projecting in its direction. A connecting passage formed between the needle carrier and a front wall of the collecting container links a flow channel with a collecting needle of a needle arrangement that is eccentric to a central longitudinal axis of the collecting chamber. As required, an openable valve arrangement is situated between the connecting passage and a collecting chamber. This valve arrangement is formed by a tube valve or flap valve disposed between the syringe and the collecting container and/or the connecting passage. The syringe is preferably set concentric to the collecting container. The flow channel feeds into the connecting passage between the syringe and an outer wall of the collecting container.

SUMMARY OF THE INVENTION

According to the present invention, a device for underpressuring collection and dosage liquid samples, in particular for analytic tests, comprises a holder with a blood sample collection tube-syringe on the one side and a needle arrangement on the other side, the holder comprises a set of two valves, the first valve on the tube-syringe's side being a tyre valve and the second valve on the side of the needle being a membrane valve which has a membrane placed on an under-support with side-inlets.

The device according to the invention further comprises a guide bar of the holder which is open on the one side and on the other side has a conic head for the needle and a seating within the guide bar, the membrane valve being placed on a side of a frontal surface of the seating and on the other side there is placed the tyre valve comprising a inner needle covered by a tyre. The membrane and the under-support are placed in a recess on the frontal surface of the seating.

The device according to the invention has also an under-membrane chamber in the seating under the membrane. The under-support has a form of a sleeve with side-inlets or is formed by a number of separate supports which are distributed in the same distance from the axis of the membrane. The thickness of the membrane is considerably smaller in its periphery than in its central part, in particular, the thickness of the membrane is smaller outside the under-support.

In the present invention the axis of the inner needle is in principle in line with the axis of the membrane and the conic head has on the seating's side a top-support of the membrane whose position is in line with the position of the under-support.

The holder, in the device according to the invention, has a shield which is placed on the guide bar of the holder and has an opening for the conic head in its top part. The shield is joined with the guide bar by upper latches and lower latches and there is a security container for the needle. The shield has in its upper part an observation window for the observation of collected liquid. Moreover, the shield and the guide bar have in their lower part an opening for the observation of a liquid material in the tube-syringe inserted into the holder, the guide bar has in its lower part a stabilising flange. In a rubber plug of the tube-syringe a cleaning chamber is placed.

In the device according to the invention, between the conic head and the needle, there is placed an opening needle head comprising a conic sleeve having a head part which is formed as the conic head of the holder and a lower part which is placed on the conic head of the holder, wherein inside of the conic sleeve in its lower part is placed an opening needle. The axis of the opening needle passes through the membrane and is in principle in line with the axis of the inner needle.

An advantage of the solution according to the present invention is a fact that after inspection of the correctly performed injection into blood vascular system or any body cavity in the observation window, the liquid material flows into the blood sample collection tube-syringe in an unconstrained manner and it cannot flow back. Moreover, the shield of the holder is a safety container for a used needle. The device according to the invention may be used also for dosage remedy liquids with an added opening needle head.

BRIEF DESCRIPTION OF THE DRAWINGS

The accompanying drawings, which are incorporated in, and form a part of the specification, illustrate an embodiment of the present invention and, together with the description, serve to explain the principles of the invention. In the drawings:

FIG. 1 shows a holder of a device for underpressuring collection and dosage liquid samples with a needle arrangement;

FIG. 2 shows the holder in section A—A in FIG. 1;

DETAILED DESCRIPTION OF THE INVENTION

Reference will now be made in detail to the preferred embodiment of the invention, an example of which is illustrated in the accompanying drawings.

Figure 3:
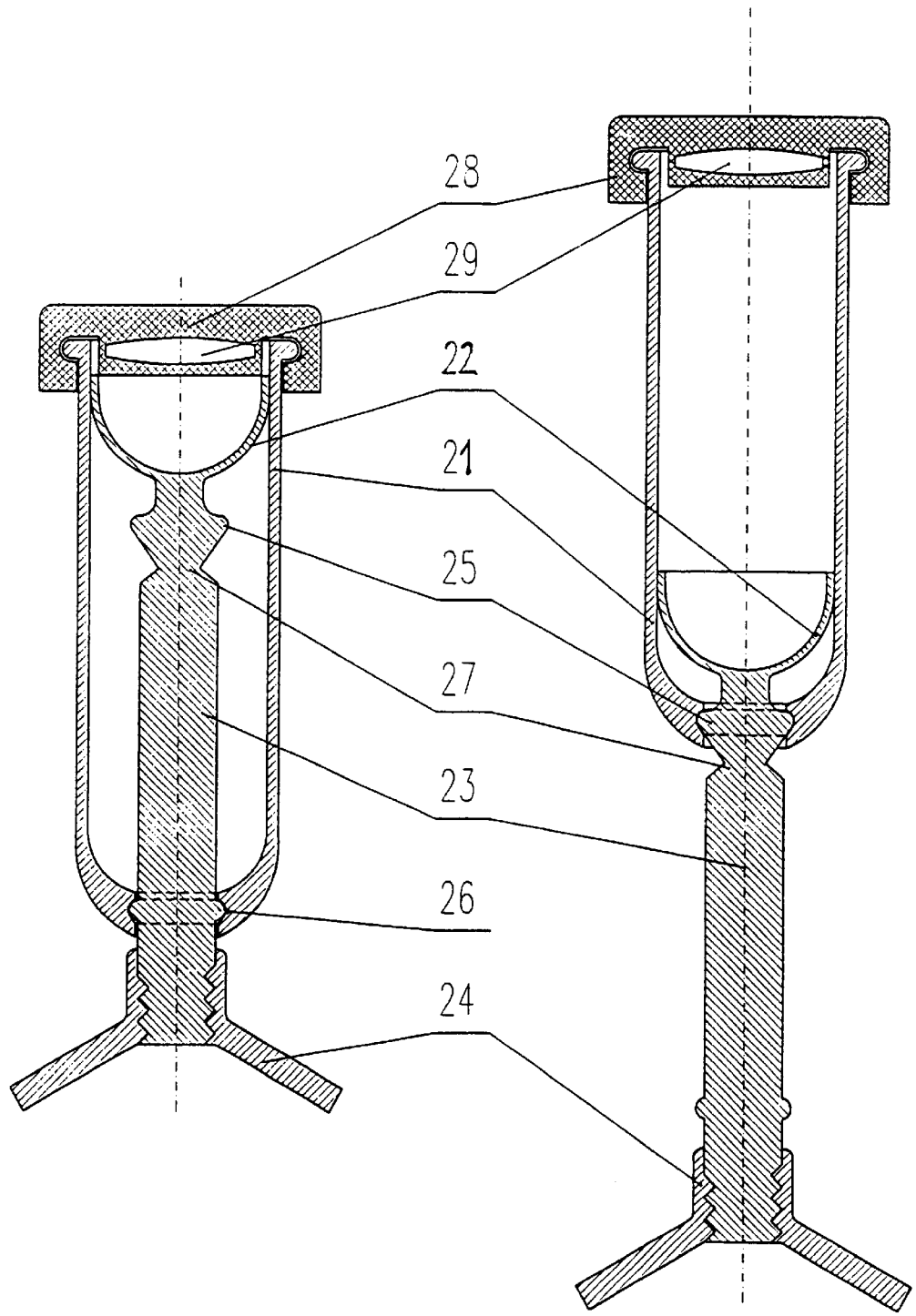
FIG. 3 shows a blood sample collection tube-syringe of the device.
Figure 4:
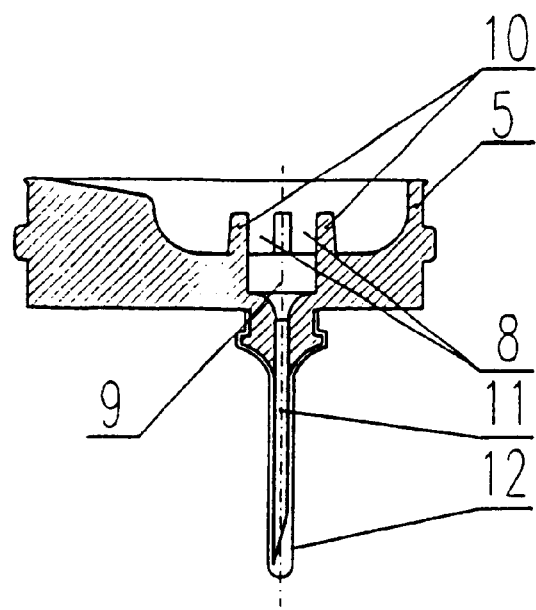
FIG. 4 shows a seating of the valve with an inner needle.
Figure 5:
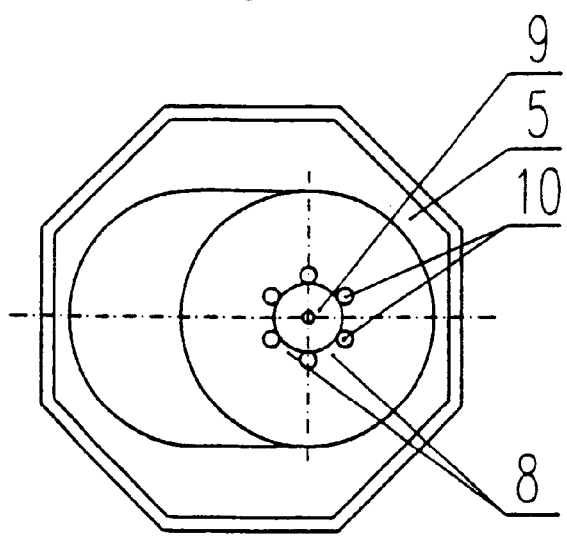
FIG. 5 shows the seating of the valve in top view.

A device for underpressuring collection and dosage liquid samples comprises three parts i.e. a holder, a blood sample collection tube-syringe on the one side of the holder and a needle arrangement on the other side of the holder. The holder comprises a set of two valves. The first valve on the tube-syringe's side is a tyre valve and the second valve on the side of the needle is a membrane valve. These parts of the device according to the invention are shown in FIGS. 1, 2 and 3. Moreover, the device comprises also an opening needle head.

The holder of the device with the needle arrangement, the construction of which is shown in FIGS. 1 and 2, comprises a guide bar (1) which is open on the one side and on the other side has a conic head (2) with an inner channel (3) for mounting the needle (4). Inside of the guide bar (1) there is mounted a seating (5) which has on its frontal surface, from the side of the conic head (2), the membrane valve. The membrane valve comprises a membrane (6) and an under-support (7) placed in a recess on the frontal surface of the seating (5) where the under-support (7) has a form of the sleeve with side-inlets (8) and it has also a under-membrane chamber (9) in the seating (5) under the membrane (6). In the preferred embodiment, the under-support (7) is formed by a number of separate supports (10) which are distributed in the same distance from the axis of the membrane (6). Moreover, the thickness of the membrane (6) on its periphery is considerably smaller than in the central part or the thickness of the membrane (6) is smaller outside the under-support (7). The seating (5), the membrane (6) and the under-support (7) with side-inlets (8) or separate supports (10) form a counter-reversible membrane valve. On the other side of the seating (5) there is placed a tyre valve comprising an inner needle (11) covered by a tyre (12) where the axis of the inner needle (11) is in principle in line with the axis of the membrane (6). The conic head (2) has, on the seating's side, a top-support (13) of the membrane (6) whose position is in line with the position of the under-support (7).

The holder of the device has further a shield (14) which is placed on the guide bar (1) of the holder and has an opening for the conic head (2) in its top part. The shield (14) is joined with the guide bar (1) by upper latches (15) and lower latches (16). The shield (14) has in its upper part an observation window (17) for observation of the liquid collected from blood vascular system or any body cavity which is collected in an initial collection liquid chamber (18) between the conic head (2) and the seating (5). The shield (14) and the guide bar (1) have in their lower part an opening (19) for observation of a liquid material in the tube-syringe inserted in the holder. Moreover, the guide bar (1) has in its lower part a stabilising flange (20).

A blood sample collection tube-syringe of the device is presented in FIG. 3. The blood sample collection tube-syringe comprises a transparent sleeve (21) wherein a piston (22) with a piston rod (23) is placed. The piston (22) is ended by a tie (24) outside the sleeve (21). The piston rod (23) has a blocking (25) which is in a cut-out (26) of the bottom of the sleeve (21) in an extreme position of the piston rod (23). Moreover, the piston rod (23) has a reduction (27) close behind the blocking (25). The second, opened end of the transparent sleeve (21) is coated by a rubber plug (28) having an inner cleaning chamber (29).

Figures 6, 7:
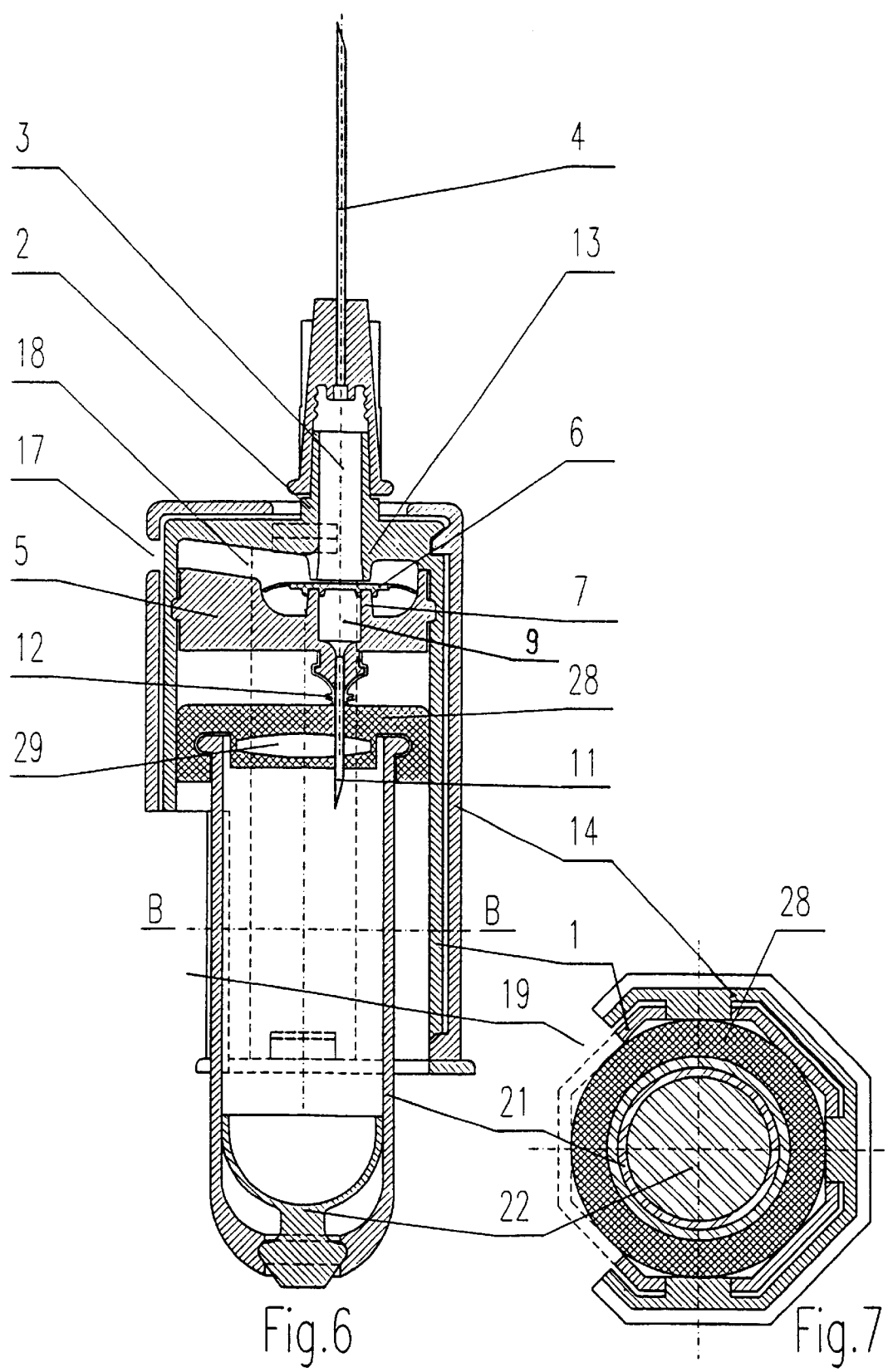
FIG. 6 shows the holder with the blood sample collection tube-syringe and the needle arrangement.
FIG. 7 shows the holder in section B—B in FIG. 6.

A complete device which is shown in FIGS. 6 and 7 comprises the holder with the blood sample collection tube-syringe and the needle arrangement. As presented, after inserting the blood sample collection tube-syringe into the holder from the opening side of the guide bar (1), the tyre (12) and the rubber plug (28) are perforated by the inner needle (11) and the inside of the sleeve (21) of the blood sample collection tube-syringe is connected with the counter-reversible membrane valve.

Figure 8:
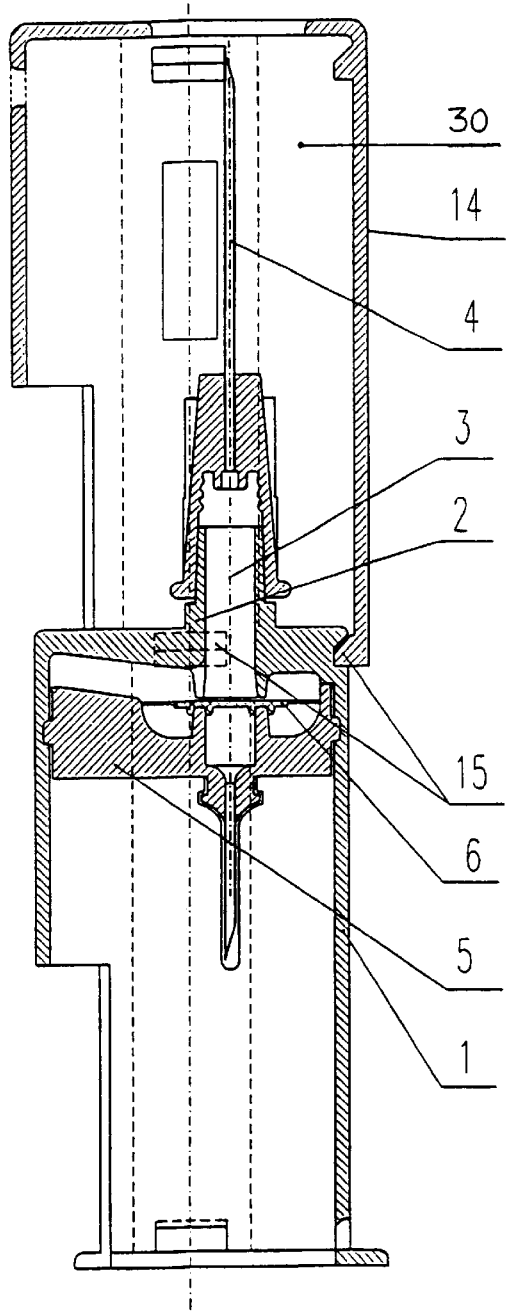
FIG. 8 shows the holder with a shield.

FIG. 8 shows the holder with the shield (14) which is joined with the guide bar (1) by upper latches (15), said shield being a security container (30) for the needle (4).

Operation of the device, which is shown in FIGS. 1 to 8, during collection of blood samples is as follows. The needle (4) is mounted on the conic head (2) and introduced into the blood vascular system or any body cavity with liquid content. A liquid sample of the blood or organism liquids collected by the needle (4) flows into the initial collection liquid chamber (18) between the top-support (13) and the membrane (6) by a culvert recess in this top-support (13). The liquid sample in the chamber (18) is observed by the observation window (17). When the liquid content is present in the chamber (18), the blood sample collection tube-syringe is introduced into the holder by the opening (19) of the shield (14) and the guide bar (1). The negative pressure created in the sleeve (21) of the blood sample collection tube-syringe by the piston (22), the piston rod (23) and the tie (24) causes the edges of the membrane (6) to deviate downwards, as it is shown in FIG. 6, and the liquid content is sucked into the sleeve (21) of the blood sample collection tube-syringe. The liquid content in the blood sample collection tube-syringe is observed in the holder through the opening (19) of the shield (14) and the guide bar (1). The blood sample collection tube-syringe with the liquid content is further removed from the holder of the device and delivered for analytic tests.

A device according to the invention may also be used for dosage liquid samples, in particular any remedy liquid. For this purpose, the remedy liquid is sucked into the blood sample collection tube-syringe. Next, the tube-syringe with the remedy liquid is placed in the holder and an opening needle head with a new needle is placed on the conic head (2) of the holder. Therefore, this device with the opening needle head placed between the conic head (2) and the needle (4) is adapted to dose the remedy liquid.

Figure 9:
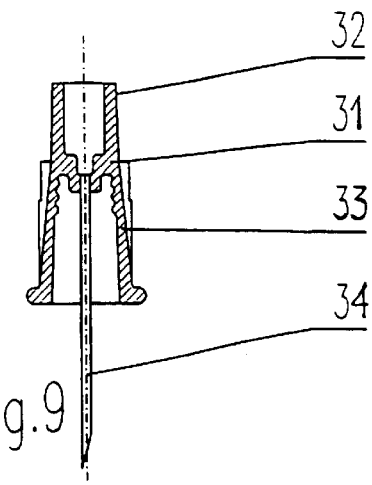
FIG. 9 shows an opening needle head.

The opening needle head, as shown in FIG. 9, comprises a conic sleeve (31) with a head part (32) which is formed as the conic head (2) of the holder and a lower part (33) which is placed on the conic head (2) of the holder, an opening needle (34) being placed inside of the conic sleeve (31), in its lower part. The axis of the opening needle (34) passes through the membrane (6) and is in principle in line with the axis of the inner needle (11).

Figure 10:
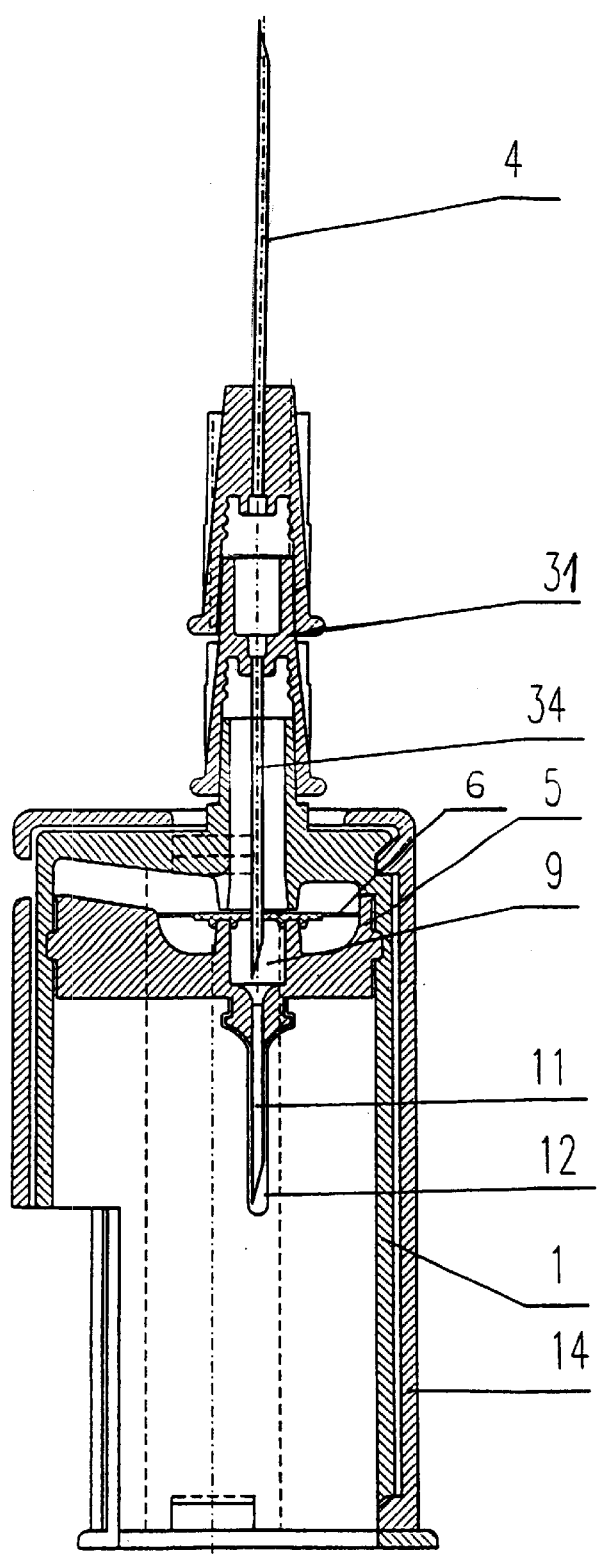
FIG. 10 shows the holder with the opening needle head.

After the opening needle head is placed on the conic head (2), as it is shown in FIG. 10, the opening needle (34) perforates membrane (6) and connects the inner needle (11) with a new needle (4) by the under-membrane chamber (9). The tube-syringe with the remedy liquid is placed in such a modified device and after perforation of the tyre (12) and opening the passage between the inside of the sleeve (21) with the remedy liquid and the new needle (4), the content of the tube-syringe is dosed by a dislodging movement of the piston (22) into the blood vascular system or any body cavity.

I claim:

1. A device for underpressuring collection and dosage liquid samples comprising a holder with a blood sample collection tube-syringe on one side and a needle on the other side, wherein the needle is mounted on a conic head of the holder, wherein the holder includes a first valve on the side with the blood sample collection tube-syringe and a second valve on the other side with the needle, wherein the first valve is a tyre valve, wherein the second valve is a membrane valve including a membrane placed on an under-support with side-inlets, wherein an opening needle head is located between the conic head and the needle, wherein the opening needle head includes a conic sleeve having a head part and a lower part, wherein the lower part of the conic sleeve is placed on the conic head of the holder, and wherein an opening needle is disposed inside of the lower part of the conic sleeve.

2. The device according to claim 1, wherein an axis of the opening needle passes through the membrane.

3. The device according to claim 1, wherein the holder includes a guide bar with an opening on one side and the conic head on the other side, wherein a seating is located within the guide bar, wherein the membrane valve is located on a frontal surface of the seating and a tyre valve comprising an inner needle covered by a tyre is located on the other surface of the seating.

4. The device according to claim 3, wherein the membrane and the under-support are placed in a recess on the frontal surface of the seating.

5. The device according to claim 3, wherein the holder includes an under-membrane chamber under the membrane in the seating.

6. The device according to claim 3, wherein an axis of the inner needle is in line with an axis of the membrane.

7. The device according to claim 3, wherein the conic head includes a top-support of the membrane, and wherein the top-support is positioned in line with a position of the under-support.

8. The device according to claim 3, wherein the holder has a shield which is placed on the guide bar of the holder, and wherein the shield has an opening for the conic head.

9. The device according to claim 8, wherein the shield is joined with the guide bar by upper latches and lower latches.

10. The device according to claim 8, wherein the shield is a security container for the needle.

11. The device according to claim 8, wherein the shield includes an observation window in an upper part of the shield for an observation of collected liquid.

12. The device according to claim 8, wherein the shield and the guide bar have an opening for observation of a liquid material in the tube-syringe inserted into the holder.

13. The device according to claim 3, wherein the guide bar has a stabilizing flange.

14. The device according to claim 3, wherein an axis of the opening needle is in line with an axis of the inner needle.

15. The device according to claim 1, wherein the under-support has a form of a sleeve with the side-inlets.

16. The device according to claim 1, wherein the under-support is formed by a number of separate supports.

17. The device according to claim 16, wherein the separate supports of the membrane are distributed a constant distance from an axis of the membrane.

18. The device according to claim 1, wherein a thickness of a periphery of the membrane is smaller than a thickness of a center of the membrane.

19. The device according to claim 18, wherein the thickness of the membrane is smaller outside the under-support.

20. The device according to claim 1, wherein a cleaning chamber is placed in a rubber plug of the tube-syringe.

* * * * *